United States Patent [19]

Adekunle et al.

[11] Patent Number: 5,431,914
[45] Date of Patent: Jul. 11, 1995

[54] METHOD OF TREATING AN INTERNAL CONDITION BY EXTERNAL APPLICATION OF CAPSAICIN WITHOUT THE NEED FOR SYSTEMIC ABSORPTION

[76] Inventors: Michael Adekunle, 1660 N. Prospect Ave., #705, Milwaukee, Wis. 53202; James L. Flowers, 10917 N. San Marino Dr., Mequon, Wis. 53092

[21] Appl. No.: 213,654

[22] Filed: Mar. 16, 1994

Related U.S. Application Data

[63] Continuation-in-part of Ser. No. 870,510, Apr. 17, 1992, Pat. No. 5,178,879, and Ser. No. 752, Jan. 5, 1993, abandoned.

[51] Int. Cl.⁶ ..................... A61K 7/00; A61K 35/78
[52] U.S. Cl. ..................... 424/401; 424/195.1; 424/DIG. 5; 514/626; 514/627; 514/817; 514/835; 514/849; 514/899
[58] Field of Search ............. 424/195.1, 401, 58; 514/817, 835, 849, 899, 626, 627

[56] References Cited

U.S. PATENT DOCUMENTS

| | | | |
|---|---|---|---|
| 4,313,958 | 2/1982 | LaHann | 424/324 |
| 4,486,450 | 12/1984 | Bernstein | 414/324 |
| 4,536,404 | 8/1985 | Bernstein | 514/627 |
| 4,546,112 | 10/1985 | LaHann et al. | 514/627 |
| 4,557,934 | 12/1985 | Cooper | 424/128 |
| 4,997,853 | 3/1991 | Bernstein | 514/626 |
| 5,008,289 | 4/1991 | Bernstein | 514/535 |
| 5,045,565 | 9/1991 | Gardner et al. | 514/487 |
| 5,134,166 | 7/1992 | Bernstein | 514/627 |

FOREIGN PATENT DOCUMENTS 3184915 8/1991 Japan.

OTHER PUBLICATIONS

Flowers et al, "Review of Capsagel ™ and Capsaicin" (1993).
Flowers et al, "Capsagel ™ Information Packet" (1993).

*Primary Examiner*—Thurman K. Page
*Assistant Examiner*—Sally Gardner
*Attorney, Agent, or Firm*—Quarles & Brady

[57] ABSTRACT

A method of treating a pathological condition of an internal organ in a patient which comprises topically applying capsaicin to the skin of the patient containing nerves which lead to the spinal cord segments corresponding to the internal organ without the need of systemic absorption of the capsaicin.

7 Claims, No Drawings

METHOD OF TREATING AN INTERNAL CONDITION BY EXTERNAL APPLICATION OF CAPSAICIN WITHOUT THE NEED FOR SYSTEMIC ABSORPTION

RELATED CASES

The present application is a continuation-in-part of our earlier U.S. patent application Ser. No. 07/870,510 filed Apr. 17, 1992, now U.S. Pat. No. 5,178,879, and U.S. patent application Ser. No. 08/000,752 filed Jan. 5, 1993, now abandoned.

FIELD OF THE INVENTION

The present invention relates to a method whereby medication is applied externally to the skin to treat an internal condition without the need for systemic absorption.

BACKGROUND OF THE INVENTION

The traditional manner of using a medication to achieve an effect on an internal condition has been to use the non-invasive routes of oral, rectal, and nasal administration, and invasive routes of intravenous, subcutaneous and intramuscular administration. All of these routes depend on the medication entering the bloodstream, reaching effective levels and then exerting its effects on the internal organ or site. The medication could be introduced at any of the available sites in relation to the internal organ—there is no requirement of a specific site of application of the medication.

The cutaneous route of administration has also been used. All known cutaneous applications of medication to achieve their desired effects have been by one of two general mechanisms. One mechanism is the direct absorption of medication into the area of pathology to achieve a desired local effect. That is, the medication is placed directly over the site where it is expected to act. The medicine then absorbs through the skin to the site. Examples include the use of topical steroids (eg, the use of triamcinolone to treat eczema), and the use of topical capsaicin for the treatment of post-herpetic neuralgia. In this method, it makes no sense or utility to place capsaicin on the left arm when the Herpes zoster is on the right arm—the medicine must be placed directly on the site it is to effect. The other accepted mechanism is to use the skin as a means of delivering medication to the systemic circulation. The medication is absorbed through the skin and into the blood stream. The circulatory system then delivers the medicine to the site of pathology. Examples of that mechanism include the use of nitroglycerin ointment to treat angina pectoris of the heart, estrogen patches which act on the uterus and catapres patches for blood pressure control which act on the brain. The site of medication application to the skin is generally independent of the target site of action. That is, the medication may be placed, more or less, randomly on the skin. Another requirement is that the topical medication must be placed on the skin in large enough amounts to be absorbed into the blood stream and reach therapeutic levels. This is accomplished by higher concentrations of the medication in a reservoir, by the use of agents which enhance the absorption of medication present, and by delivery devices which control the rate of absorption such that overdose or dumping of the medicine does not occur. So, for a topical nitroglycerin patch to treat angina of the heart, an internal organ, the patch does not have to be placed over the heart. In fact the patch can be placed anywhere on the skin, no specific site is required. The only goal is to have as much of the medication as possible absorb through the skin and reach therapeutic blood levels at the heart.

The method of the present invention is distinctly different from all of the above methods and specifically different from the traditional methods of use of topical medications. None of the methods above require a specific site of application, or injection, to treat an internal organ condition. Our method requires a specific site of application to treat a distant internal organ. Whereas all of the above conditions require a systemic blood level to achieve its effect on an internal organ, our method does not require blood levels and, in fact, uses dosages of capsaicin which are far less than those used for systemic effects. Whereas our method requires specific topical application of capsaicin for effectiveness, that application is not directly on the site of its intended effect and is not directly on the site of pathology. All of these differences show the uniqueness of this invention.

Capsaicin (trans-8-methyl-N-vanillyl-6-nonenamide), the pungent principle of red peppers, has been used cutaneously for the treatment of pain. Synthetic capsaicin (nonyl vanillylamide) acts in the same manner as capsaicin, and capsaicin (more properly capsaicinoids) is meant to include this substance for brevity. Capsaicin is believed to act on a subset of primary afferent nerves mostly of the C fiber type (polymodal, thin, unmyelinated), although some A delta (thin, myelinated) are also capsaicin sensitive. Capsaicin is believed to bind to a receptor at the nerve ending and cause a release of a variety of neuropeptides (e.g., substance P,CGRP and others) and results in afferent nerve conduction initially. There are two main phases of action, first an excitation and then a desensitization of the nerve to stimulation. The excitation results in the 'hot' of hot pepper or the burning tingling sensation which can occur when capsaicin is applied to the skin. The desensitization results from the depletion of neuropeptides and interference with afferent conduction in a non-tetrodotoxin dependent manner. It has been demonstrated that topically (skin) applied capsaicin can deplete neuropeptides at the peripheral (cutaneous) and central (dorsal horn of spinal cord) endings of the peripheral cutaneous nerve. To date patents and articles have only described the use of capsaicin to treat cutaneous conditions (e.g., psoriasis or post-herpetic neuralgia), neuropathic conditions affecting the skin or subcutaneous area (e.g., postmastectomy neuroma or diabetic neuropathy) or direct subcutaneous conditions (e.g., osteoarthritis or rheumatoid arthritis). All of these treatments use the cutaneous application of the capsaicin to affect direct subcutaneous pathology (i.e., the local effect). These methods require direct application at the site of pathology (i.e., no internal conditions).

It is believed that no method of treatment has been described in the literature which employs the isolated topical application of capsaicin to the skin to achieve systemic effects for an internal condition distant from the site of application. Furthermore, no literature or available medicine was found which describes the treatment of an internal condition by topical application of that medication which did not require systemic absorption of the medication. Capsaicin has only been applied directly over the site of pathology for its therapeutic uses. The application of a medication at a specific skin site in amounts that cannot achieve significant systemic blood levels to treat a distant internal site of pathology has not been done—this invention is truly unique and unexpected.

DEFINITION OF TERMS

CAPSAICIN, NATURAL—Capsaicin is derived from the fruits of the Solanaceae family and the Capsicum genus. The crude isolate of the fruit is called capsicum oleoresin and contains over 100 chemicals. A further extraction process results in 'natural capsaicin'. This isolate contains up to 5 related molecules which are capsaicin, dihydrocapsaicin, nordihydrocapsaicin, homocapsaicin and homodihydrocapsaicin 1. Most of this 'natural capsaicin' is made of capsaicin and dihydrocapsaicin. The 'natural capsaicin' was used in our trials. When capsaicin (more properly capsaicinoids) is used herein, it is meant to include these five molecules and synthetic capsaicin as described below. The compounds are:

CAPSAICIN(N-[(4-hydroxy-3-methoxyphenyl)methyl]-8-methyl-(E)-6-nonenamide) or (trans-8-methyl-N-vanillyl-6-nonenamide)
CAS REGISTRY NUMBER—404-86-4
MOLECULAR FORMULA—$C_{18}H_{27}NO_3$
MOLECULAR WEIGHT—305.4amu
DIHYDROCAPSAICIN(N-[(4-hydroxy-3-methoxyphenyl)methyl]8-methylnonanamide)
CAS REGISTRY NUMBER-19408-84-5
MOLECULAR FORMULA—$C_{18}H_{29}NO_3$
MOLECULAR WEIGHT—307.4amu CAPSAICINOIDS —The capsaicinoids are compounds with action like capsaicin. These include the natural products (under Capsaicin, Natural) and the synthetic (under Capsaicin, Synthetic).

CAPSAICIN, SYNTHETIC—Synthetic capsaicin is present in the natural plants but in small amounts. It is sold as a capsaicin substitute. It also affects the CSPA's just like capsaicin. It has been used in our trials and has been effective. For convenience, the term capsaicin (actually capsaicinoids) used herein is meant to encompass both the natural capsaicin as discussed above and the synthetic capsaicin. The details for 'synthetic capsaicin' are:

NONIVAMIDE(N-[(4-hydroxy-3-methoxyphenyl)-methyl]nonanamide)
OTHER COMMON NAMES-Pelargonic acid vanillylamide Nonylic acid vanillylamide
CAS REGISTRY NUMBER—2444-46-4
MOLECULAR FORMULA—$C_{17}H_{27}NO_3$
MOLECULAR WEIGHT—293.4amu CAPSAICIN when used by itself includes capsaicin, natural; capsaicinoids; and capsaicin, synthetic.

CSPA—CSPA stands for capsaicin sensitive primary afferents. CSPA are nerves which are sensitive to capsaicin. These are found in the nerves to the skin and to many internal organs. CSPA's are discussed in the following reference which is included in its entirety herein: Maggi and Meli, *The Sensory Efferent Functions of Capsaicin Sensitive Neurons.* Gen Pharmac 1988;19:1–43.

DAB OF CAPSAICIN—An approximate average dose application for use in this discussion. It is a spherical amount 5 mm (0.5 cm) in diameter. Its volume would be 0.0654 cc (cubic centimeters) or ml (milliliter). The density is approximately 1 g/ml so the weight would also be 0.0654 g (grams) of the vehicle. This would mean there are approximately 0.00003 g of capsaicin in a 'dab' of 0.05% capsaicin (W/W). This is equivalent to 0.03 mg (milligrams) of capsaicin per 'dab'.

DERMATOME—A dermatome is the skin representation of the distribution of spinal nerves (or cranial nerves) upon the skin. Due to changes from a quadruped to a biped gait, the human dermatomes are not simply one to one representations on the human body surface. Also, peripheral nerves may ascend or descend once reaching the spinal cord and overlap does result. Each of the spinal nerves comes from a specific spinal cord segment based on embryological development. Other nerves, based on embryological development communicate with the body's internal organs on a spinal cord segmented basis. So, each internal organ has a skin representation, according to its embryologic origin, in one or more dermatomes. A similar arrangement exists for cranial nerves. So, there are relatively consistent dermatomal representations of internal organs on the human body surface. When dermatome is used herein, it is meant to describe these constant relationships with the understanding that some minor variations do not detract from the site specifics as described. Further discussion can be found in the latest edition of Gray's Anatomy.

TOPICAL MEDICATION FOR LOCAL EFFECT—This is a medication which is applied to the skin and acts directly at the site of application. It must be placed at the site of pathology, and it directly absorbs through the skin and exerts its effect. There is no systemic absorption needed for the effect to occur.

TOPICAL MEDICATION FOR SYSTEMIC EFFECT—This is a medication which is applied to the skin and acts at a site distant from the site of application. The medication may be applied anywhere on the body and achieve its effect. The medication must absorb through the skin, enter the bloodstream, reach effective levels in the blood, and then travel to its site of action to exert its effect.

SUMMARY OF INVENTION

It is an object of the present invention to disclose a method which comprises externally applying capsaicin to the skin to treat an internal condition distant from the site of application without requiring systemic absorption of capsaicin.

It has been discovered that the external application of capsaicin to the skin affects certain nerves (called capsaicin sensitive primary afferents-CSPA) in the skin which lead to spinal cord segments which affect certain internal organs. These CSPA nerves are also found in a large number of internal organs including the lung, heart, bladder, uterus and gastrointestinal tract. A large variety of neuropeptides have been associated with these nerves including substance P, CGRP, galanin, somatostatin and others.

We have discovered that the topical external application of capsaicin to the areas of the skin containing CSPA can be used to treat the symptoms of pathological conditions arising from certain internal organs served by CSPA's. These include pathological conditions of the gastrointestinal tract, the lung, female pelvic structures and internal orofacial structures such as the teeth among others.

As previously noted, the term 'capsaicin' used herein is meant to include capsaicin, natural, the components of isolated capsaicinoids and capsaicin, synthetic, (see definitions).

The mechanism of action of this invention is via special nervous pathways and is independent of systemic absorption. That is, this method does not require the capsaicin to be absorbed into the systemic circulation to reach therapeutic levels and then affect the internal organ. The method allows rapid, safe and effective treatment of internal conditions without the necessity of systemic distribution of medication. The invention was unexpectedly discovered during trials of using capsaicin to treat musculoskeletal back pain when it was noted that the patient also achieved significant relief of a coexisting intrapelvic condition.

The unexpectedness of this discovery and the evolving knowledge of capsaicin and CSPA nerves do not provide a completely clear mechanism of how this invention works. However, it is felt that the beneficial effects, which include but are not limited to the relief of pain, are due to the cutaneous application of capsaicin to the cutaneous nerve afferents and that the capsaicin interferes with the visceral afferent CSPA at the level of the spinal cord. It is well-known that pain from internal structures is often felt in the dermatome corresponding with the embryological origin of the organ. It has been postulated that the cutaneous and visceral afferents converge upon common projection neurons in the spinal cord. It is at this point interactions can occur between internal and external structures. Although, all details are not clear, the above relationships might partly explain the mechanism of action of this discovery.

Of particular importance to this discovery is that the effect of the topical application is not to achieve systemic absorption.

If the effect occurred simply by systemic absorption, the application could be anywhere on the skin as for well-known topically applied but systemically working medications. The specificity of application of the capsaicin to selected areas of skin to affect specific internal organs is an important feature of this invention.

The amounts of capsaicin used in the invention preclude any possibility of significant systemic therapeutic blood levels. In the LaHann U.S. Pat. No. 4,313,958, systemic injections of capsaicin were used to achieve systemic analgesia using capsaicin. In one series of tests on rats (Column 3, lines 27–33), it required capsaicin injected systemically at 50 mg/kg to elevate the pain threshold. It later notes (Column 6, lines 48–50), that analgesic effects in humans will require 0.5 mg/kg to 50 mg/kg. Based on these numbers for human analgesia using the 0.05% capsaicin gel (remember that topical medicines are often not 100% absorbed as for an injected medicine), the following amounts of gel would have to be topically applied to the skin to achieve analgesia at an internal site (these calculations are based on a 50 kg human which is small for many of our patients 75–125 kg patients are common):

| Dosage amount required | Grams of 0.05% capsaicin gel required |
|---|---|
| 0.5 mg/kg | 50 grams |
| 5.0 mg/kg | 500 grams |

This means to deliver the lower 'especially preferred dose' of capsaicin topically would require the application of 50 grams of the vehicle to the skin. Since one ounce is 28.35 grams, this means 50 grams is 1.76 ounces. This means more than a whole tube of a commercially available cream (Zostrix by Gen Derm, 0,025%, 1.5 ounces costing $20.00 to $30.00) would have to be applied to achieve appropriate systemic levels. Besides the dollar costs, the burning sensation on the skin would preclude this. The amount of our gel (0.05% capsaicin) typically applied is a 5 mm diameter dab (see the definition of terms). This is a volume of 0.0654 ml or 0.0654 grams (approx.). The amount of capsaicin in this dab is 0.00003 grams or 0.03 mg. Applying one dab to a 50 kg person then yields a dose of:

$$\frac{0.03 \text{ mg capsaicin}}{50 \text{ kg body weight}} = 0.0006 \text{ mg/kg}.$$

This value is magnitudes below the lowest limits of LaHann for systemic levels of capsaicin. Even if ten dabs were used, the dosage is still too low (0.006 mg/kg) for systemic effects. The mechanism of our invention's effectiveness is not by systemic absorption. Following are the skin application sites for treating various internal organ pathologies.

1) Pathological conditions of teeth, gums and oral mucous membranes, such as toothache.

Upper regions—apply to the skin over the maxillary division of the trigeminal nerve; a region including upper lips to the angle of the mouth, lower lateral nose to temporal area just lateral to the eye; and/or from midline face laterally for each side of face.

Lower regions—apply to the skin over the mandibular division of the trigeminal nerve; a region from the lower lip to chin area to the corner of the mouth to the temporal region just anterior to the ear; and/or from the midline of the face laterally for each side of the face.

2) Pathological conditions of the lung and tracheobronchial tree such as cough or dry cough.

Apply to the skin over the spinal nerves C1 through T9, to their anterior and posterior cutaneous divisions; application is anteriorly from the level of the ramus of the mandible to the area just above the umbilicus; the preferred anterior area is from the sternal notch superiorly to the xiphisternum inferiorly and then laterally along the inferior rib margins and cephalad to the lateral border of the clavicle; posteriorly the application is from the nape of the neck to the mid to lower dorsal spine medially and laterally.

3) Pathological conditions of the stomach such as gastroesophageal reflux disease symptomology.

Apply to the skin over the spinal nerves T4 through T10, to their anterior and posterior divisions; the preferred application is from the nipple line to an area midway between the lower rib margins and the umbilicus to include the epigastric region and laterally to the midaxillary line; the application can be applied to the back in approximately the mid-third of the thoracic spine region; applications are focused on the left half of the body.

4) Pathological condition of the esophagus

Apply to the skin over the spinal nerves C6 through T5 to their anterior and posterior divisions; the application is preferably to the anterior midline from the sternal notch to the epigastrium and extending several inches to either side of the midline; application may also be to the lower cervical to mid thoracic spine extending several inches to either side of the midline.

5) Pathological conditions of the small intestines such as gastroenteritis.

Apply to the skin over the spinal nerves T9 through T12 to the anterior and posterior divisions; the preferred area is a wide circular region with the umbilicus as the center extending outward toward the epigastrium, the flanks and suprapubic region; application may also be to the back in a broad rectangular region centered at about the level of the umbilicus (anteriorly).

6) Pathological conditions of the large intestine/rectosigmoid such as irritable bowel syndrome.

Apply to the skin over the spinal nerves T12 through S3 to their anterior and posterior divisions; the preferred application is to a large oval region with its upper margin just below the umbilicus and its lower margin near the pubic bone and extending laterally to the iliac crests; also may apply to the skin posteriorly in a region centering on the midline and extending laterally in both directions with the upper margins at approximately the upper limits of the iliac crests and the lower margins at the level of the coccyx.

7) Pathological conditions of the female pelvic structures such as abdominal muscle cramps and endometriosis.

Apply to the skin over the spinal nerves T10 through S4 to their anterior and posterior divisions; preferred area of application is anteriorly from the umbilicus to the superior margins of the pubic bone, and posteriorly from the approximate level of the umbilicus (anteriorly) and to the lower lumbar vertebrae with wide lateral extensions from the midline; other areas of application include the skin over the pubic area anteriorly, the inner upper thigh area bilaterally and the sacral region posteriorly.

Although not specifically evaluated, it is within the scope of the invention to treat other internal organs in a similar manner. These include the intracranial vessels, the heart, the liver and biliary tract, the pancreas, the sinuses and nasal mucosa and the kidney/bladder and ureter as examples.

It will be apparent to those skilled in the art that aforementioned objects and advantages, as well as others, are obtainable by practice of the present invention.

DESCRIPTION OF THE PREFERRED EMBODIMENT

In the preferred practice of the method of the present invention a gel containing a safe and effective amount of capsaicin is topically applied to the area of the skin containing the CSPA nerves which correspond to the spinal cord segments of the target internal organs.

EXAMPLES The following examples illustrate the method of treatment of the present invention.

EXAMPLE 1

A female in her 30's was visiting from Alaska. A prior root canal filling was suddenly dislodged. There was sudden increased pain. Aspirin was tried without relief. The tooth was a molar in the right lower posterior quadrant. A 'dab' (see definition of terms) of 0.05% capsaicin gel (Capsagel TM, Iyata Pharmaceutical, Milwaukee, Wis.) was applied to and rubbed into the skin over the location of the tooth and the pain-none was applied to the tooth or the gums. Relief occurred rapidly and was nearly complete. Four hours later, she was able to see a dentist who performed some invasive work and replaced the filling. No additional anesthesia was required.

EXAMPLE 2

A 43 year old female mother of four had the onset of severe cramps beginning within one year of menses onset at age 12. The patient had frequent, severe and debilitating menses often resulting in days off work and school, and often requiring bedrest. She had used Tylenol ES (500 mg, four at one time) with minimal relief; various nonsteroidal anti-inflammatory drugs (NSAIDs) with borderline relief and Ponstel with adequate relief. Relief with these medications was often delayed for 2 or more hours. The patient applied 0.05% capsaicin gel (Capsagel), approximately two 'dabs' to the skin of the lower abdomen and back areas and rubbed it in. Relief of pain in the abdomen and back occurred within 10–15 minutes and was described as complete. Also, some of the malaise and irritability subsided. The effect persisted for 12–18 hours. Repeat applications during subsequent menses provided similar relief.

EXAMPLE 3

A 45 year old male had a 15–20 year history of esophageal reflux. Symptoms were so severe, at one time, a cardiologist was consulted and a thallium stress test ruled out coronary heart disease. Pepcid at 40 mg at breakfast was begun, and symptom relief followed within a few days. After the Pepcid was stopped, the symptoms recurred periodically especially after dietary indiscretions. Usually an antacid was taken to relieve the symptoms. Instead of the antacid, a 'dab' of 0.05% capsaicin (Capsagel) was applied to the sternal, throat and epigastric areas and rubbed in. The symptoms waned within 5 minutes and were gone by 15 minutes. Lying prone and belching, which normally worsen the symptoms, had no effect. Relief persisted until a Pepcid was taken several hours later. Repeat applications on other occasions provided similar relief.

EXAMPLE 4

A 63 year old female had the symptoms of a flu syndrome. These included low grade fever, malaise, rhinorrhea and a non-productive cough. Instead of using her usual OTC cough preparation, about a 'dab' of 0.05% capsaicin (Capsagel) was applied to the anterior chest area and rubbed in. Within 30 minutes, the cough disappeared and did not return for the next 18 hours. Most of the other flu symptoms did persist.

EXAMPLE 5

A 20 year old female had eaten a barbecue dinner several days earlier, which also included potatoes and sour cream. Within one day, she had the onset of gastrointestinal upset, which included nausea but no vomiting, loose but non-watery and non-bloody bowel movements, low grade fever and abdominal pains. The pain was periumbilical, constant and with episodes of worsening. It was described as a sharp constant ache and 'like bricks' in the stomach and it was worsened by eating. About 1–2 'dabs' of 0.025% capsaicin gel (Capsagel) was applied in a wide area around and including the umbilicus and lower abdomen and rubbed in until it disappeared. The constant ache began to subside within 5–10 minutes and was gone within 30 minutes. The nausea also subsided. After about three hours a mild pain reoccurred and another 1–2 'dabs' of 0.025% capsaicin gel was applied as before. The pain was promptly relieved. No further applications were needed. Over the next few days, she was able to progress from liquid to solid foods. She had some loose bowel movements, some low grade fever and some tolerable pain, not requiring reapplication of the gel, which occurred with eating. By three days after the first application of the gel, all symptoms had subsided. The nausea and the severe pains had subsided within the two capsaicin applications.

EXAMPLE 6

A 63 year old female had the first onset of abdominal pains in her 40's. The symptoms included severe abdominal cramps in the lower abdomen, low backaches, mostly constipation and transient relief of pain after bowel movements. She had undergone a hysterectomy and laparotomy with no relief of symptoms. A colonoscopy discovered a 2 cm polyp which was removed and was benign. No other organic cause was found, as extensive gastroenterological evaluations had been done. A diagnosis of irritable bowel syndrome was made. She had used oral liquid antacids, acetaminophen and laxatives with minimal relief of symptoms. The pain was present nearly daily. One to two 'dabs' of 0.05% capsaicin (Capsagel) was applied on the skin of the lower back and lower abdomen and rubbed in at various times over a two month period. The back and abdominal pains were essentially resolved. Relief would occur within 15 minutes and would last the rest of the day. There has been no adverse effects. An adult daughter, who lives with the patient, has remarked about the absence of moaning she had observed in her mother.

EXAMPLE 7

A 51 year old female physician had longstanding endometriosis. She has required the use of narcotics in the past but has had problems with the side effects. One to two 'dabs' of 0.05% capsaicin gel (Capsagel) was applied to the skin of the mid to lower abdominal and low back areas and rubbed in. Adequate relief of symptoms has occurred on repeated applications decreasing the need for narcotic analgesics.

These are examples to illustrate the conditions we have treated. There are many more patients who have been successfully treated by the method described.

Any topical preparation containing a concentration of capsaicin of about 0.01% to about 0.1% can be used. However, preparations containing about 0.025% to 0.075% are preferred. The preparation may be a gel, cream, ointment, suspension, spray, lotion, roll-on, gel stick or patch. Plasters are not an appropriate vehicle because they limit the natural absorption. No special absorption enhancers are required-the natural absorption is all that is typically required.

The capsaicin containing topical preparation especially preferred for use in the present invention are the 0.025%, 0.05% and 0.075% capsaicin gels, available under the trademark, Capsagel ™, which is distributed by Iyata Pharmaceuticals, Inc. of Milwaukee, Wis.

It will be readily apparent to those skilled in the art that a number of changes and modifications can be made without departing from the spirit and scope of the invention. Therefore, it is intended that the invention be limited only by its claims.

We claim:

1. A method of treating a condition selected from cough and dry cough of the lungs in a patient having that condition which comprises topically applying a preparation selected from an ointment, gel, cream, suspension, gel stick, roll-on and a spray containing 0.01% to 0.1% capsaicin to the patient's skin over the spinal nerves C1 through T9, to their anterior and posterior cutaneous divisions; said preparation being applied anteriorly from the level of the ramus of the mandible to the area just above the umbilicus from the sternal notch superiorly to the xiphisternum inferiorly and then laterally along the inferior rib margins and cephalad to the lateral border of the clavicle and posteriorly from the nape of the neck to the mid to lower dorsal spine medially and laterally over the patient's back to effect treatment of said condition.

2. A method of treating gastroenteritis of the small intestine in a patient having such gastroenteritis which comprises topically applying a preparation selected from an ointment, gel, cream, suspension, gel stick, roll-on and a spray containing 0.01% to 0.1% capsaicin to the patient's skin over the spinal nerves T9 through T12 to the anterior and posterior divisions including a circular region with the umbilicus as the center extending outward toward the epigastrium, the flanks and suprapubic region or the patient's back in a rectangular region centered at about the level of the umbilicus to effect treatment of said gastroenteritis.

3. A method of treating irritable bowel syndrome in a patient having irritable bowel syndrome which comprises topically applying a preparation selected from an ointment, gel, cream, suspension, gel stick, roll-on and a spray containing 0.01% to 0.1% capsaicin to the patient's skin over the spinal nerves T12 through S3 to their anterior and posterior divisions including a oval region with its upper margin just below the umbilicus and its lower margin at about the pubic bone and extending laterally to the iliac crests or to the skin posteriorly in a region centering on the midline and extending laterally in both directions with the upper margins at about the upper limits of the iliac crests and the lower margins at the level of the coccyx to effect treatment of the irritable bowel syndrome.

4. A method of treating toothache in a patient having a toothache which comprises topically applying a preparation selected from an ointment, gel, cream, suspension, gel stick, roll-on and a spray containing 0.01% to 0.1% capsaicin applied to the patient's skin over the maxillary division of the trigeminal nerve; a region including upper lips to the angle of the mouth, lower lateral nose to temporal area just lateral to the eye; and/or from midline face laterally for each side of face or to the skin over the mandibular division of the trigeminal nerve; a region from the lower lip to chin area to the corner of the mouth to the temporal region just anterior to the ear; or from the midline of the face laterally for each side of the patient's face to effect treatment of said toothache.

5. A method of treating gastroesophageal reflux disease symptomology in a patient having that condition which comprises topically applying a preparation selected from an ointment, gel, cream, suspension, gel stick, roll-on and a spray containing 0.01% to 0.1% capsaicin to the patient's skin over the spinal nerves T4 through T10, to their anterior and posterior divisions from the nipple line to an area midway between the lower rib margins and the umbilicus to include the epigastric region and laterally to the midaxillary line or the capsaicin can be applied to the back in about the mid-third of the thoracic spine region; said applications being focused on the left half of the patient's body.

6. The method of claim 5 in which the preparation is also applied to the patient's skin over the spinal nerves C6 through T5 to their anterior and posterior divisions to the skin from an anterior midline from the sternal notch to the epigastrium and extending to either side of the midline or to the lower cervical to mid thoracic spine extending to either side of the midline.

7. A method of treating endometriosis in a patient having that condition which comprises topically applying a preparation selected from an ointment, gel, cream, suspension, gel stick, roll-on and a spray consisting essentially of 0.01% to 0.1% capsaicin to the patient's skin over the spinal nerves T10 through S4 to their anterior and posterior divisions; including anteriorly from the umbilicus to the superior margins of the pubic bone, and posteriorly from about the level of the umbilicus and to the lower lumbar vertebrae with lateral extensions from the midline or the skin over the pubic area anteriorly, the inner upper thigh area bilaterally and the sacral region posteriorly to effect treatment of said condition.

* * * * *